US012571045B2

(12) United States Patent
Hwang et al.

(10) Patent No.: US 12,571,045 B2
(45) Date of Patent: Mar. 10, 2026

(54) PAPER-BASED, NUCLEIC ACID-DETECTING KIT AND METHOD FOR ANALYSIS OF PCR AMPLICON

(71) Applicants: THE ASAN FOUNDATION, Seoul (KR); UNIVERSITY OF ULSAN FOUNDATION FOR INDUSTRY COOPERATION, Ulsan (KR)

(72) Inventors: Sang-hyun Hwang, Seoul (KR); Heung-bum Oh, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 1151 days.

(21) Appl. No.: 17/263,979

(22) PCT Filed: Jul. 22, 2019

(86) PCT No.: PCT/KR2019/009021
§ 371 (c)(1),
(2) Date: Jan. 28, 2021

(87) PCT Pub. No.: WO2020/027479
PCT Pub. Date: Feb. 6, 2020

(65) Prior Publication Data
US 2022/0195543 A1     Jun. 23, 2022

(30) Foreign Application Priority Data
Jul. 31, 2018     (KR) ........................ 10-2018-0089182

(51) Int. Cl.
*C12Q 1/6883*     (2018.01)
*C12Q 1/70*     (2006.01)

(52) U.S. Cl.
CPC ........... *C12Q 1/6883* (2013.01); *C12Q 1/708* (2013.01); *C12Q 2563/149* (2013.01);
(Continued)

(58) Field of Classification Search
None
See application file for complete search history.

(56) References Cited

U.S. PATENT DOCUMENTS 7,867,780 B2 *     1/2011     Jones ..................... B82Y 10/00
436/805

FOREIGN PATENT DOCUMENTS

JP          2017536805 A     12/2017
KR     20080077383 A     8/2008
(Continued)

OTHER PUBLICATIONS

Rinko et al Biophysical Journal. 2004. 86: 544-554 (Year: 2004).*
(Continued)

*Primary Examiner* — Carla J Myers
(74) *Attorney, Agent, or Firm* — Riverside Law LLP

(57) ABSTRACT

The present invention provides a paper-based, nucleic acid-detecting sensor capable of easily and simply detecting the presence of a target nucleic acid from a PCR amplicon. In addition, the present invention provides a paper-based, nucleic acid-detecting kit capable of easily and simply detecting the presence of a target nucleic acid from a PCR amplicon and a nucleic acid detecting method using same. The present invention can easily and simply determine the presence or absence of a target nucleic acid in a PCR amplicon by utilizing the function in which the target nucleic acid is associated with nanoparticles to form a composite and when loaded into the sensor, the composite is separated
(Continued)

and moves according to the structure of the sensor and is finally visualized on the sensor.

11 Claims, 4 Drawing Sheets

Specification includes a Sequence Listing.

(52) U.S. Cl.
CPC ... *C12Q 2563/155* (2013.01); *C12Q 2565/50* (2013.01); *C12Q 2565/518* (2013.01); *C12Q 2565/537* (2013.01)

(56) References Cited

FOREIGN PATENT DOCUMENTS

| | | | |
|---|---|---|---|
| KR | 20080104116 A | 12/2008 | |
| KR | 20160018479 A | 2/2016 | |
| KR | 20170061533 A | 6/2017 | |
| WO | 2005056827 A1 | 6/2005 | |
| WO | 2017098521 A1 | 6/2017 | |

OTHER PUBLICATIONS

Yang et al Sensors & Actuators: B. Chemical. Jan. 28, 2019. 286: 101-103 and Supplementary Data, 4 pages (Year: 2019).*
Ahern, H. The Scientist. Jul. 1995. 9(15): 20-25 (Year: 1995).*
Wikipedia®. "Sepharose", printed on Oct. 15, 2024, available via URL: < en.wikipedia.org/wiki/Sepharose> (Year: 2024).*
Cytvia. "Whatman Fusion 5", printed on Oct. 15, 2024, available via URL: <cytivalifesciences.com/en/us/shop/lab-filtration/immunodiagnostics/lateral-flow-pads/fusion-5-p-00787> (Year: 2024).*
Ahmed, Snober et al: "Paper-based chemical and biological sensors: Engineering aspects", Biosensors and Bioelectronics, Elsevier Science Ltd, UK, Amsterdam , NL, vol. 77, Sep. 25, 2015 (Sep. 25, 2015), pp. 249-263, XP029311795, ISSN: 0956-5663, DOI: 10.1016/J.BIOS.2015.09.038.
Chinga et al., "Controlled serial grinding for high-resolution three-dimensional reconstruction", The Royal Microscopical Society Journal of Microscopy August, Jan. 1, 2004 (Jan. 1, 2004), pp. 13-21, XP055902647, Retrieved from the Internet: URL:https://doi.org/10.1111/j.0022-2720.2004.01288.x [retrieved on Mar. 17, 2022].
Extended European Search Report for App. No. EP19843369.0, dated Mar. 28, 2022, 7 pages.
Wang, Jingyun et al: "Morphology and Entrapped Enzyme Performance in Inkjet-Printed Sol-Gel Coatings on Paper", Chemistry of Materials, vol. 26, No. 5, Feb. 20, 2014 (Feb. 20, 2014), pp. 1941-1947, XP055902637, US ISSN: 0897-4756, DOI: 10.1021/cm500206s.
Wei Yin Lim et al: "Microfluidic paper-based analytical devices for potential use in quantitative and direct detection of disease biomarkers in clinical analysis", Journal of Chromatography B, Elsevier, Amsterdam, NL, vol. 1060, Jun. 23, 2017 (Jun. 23, 2017), pp. 424-442, XP085184783, ISSN: 1570-0232, DOI: 10.1016/J.JCHROMB.2017.06.040.
Zhang, Daohong: "A paper-based device for double-stranded DNA detection with Zif268", AIP Conference Proceedings, vol. 1839, Jan. 1, 2017 (Jan. 1, 2017), XP055902635, New York, US ISSN: 0094-243X, DOI: 10.1063/1.4982427 Retrieved from the Internet: URL :https://doi.org/10.1063/1.4982427>.

* cited by examiner

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: HPV 16 DNA forward primer

<400> SEQUENCE: 1
ttgttggggt aaccaactat ttgttactgt t                           31

<210> SEQ ID NO 2
<211> LENGTH: 29
<212> TYPE: DNA
<213> ORGANISM: Artificial Sequence
<220> FEATURE:
<223> OTHER INFORMATION: HPV 16 DNA reverse primer

<400> SEQUENCE: 2
cctccccatg tctgaggtac tccttaaag                              29

<210> SEQ ID NO 3
<211> LENGTH: 25
<212> TYPE: DNA
<213> ORGANISM: Artificial Sequence
<220> FEATURE:
<223> OTHER INFORMATION: HPV forward primer

<400> SEQUENCE: 3
tgtcagaacc atatggcgac agctt                                  25

<210> SEQ ID NO 4
<211> LENGTH: 25
<212> TYPE: DNA
<213> ORGANISM: Artificial Sequence
<220> FEATURE:
<223> OTHER INFORMATION: HPV reverse primer
```

-continued

<400> SEQUENCE: 4
ttcaccaaca gcaccagccc tatta                                        25

PAPER-BASED, NUCLEIC ACID-DETECTING KIT AND METHOD FOR ANALYSIS OF PCR AMPLICON

CROSS-REFERENCE TO RELATED APPLICATIONS

This application is the U.S. national phase application filed under 35 U.S.C. § 371 claiming benefit to International Patent Application No. PCT/KR2019/009021, filed on Jul. 22, 2019, which claims priority to Korean Patent Application No. 10-2018-0089182, filed Jul. 31, 2018, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0111-00US_Sequence_Listing_v2_ST25.txt" in ASCII format. The text file containing the Sequence Listing of the present application was created on Aug. 31, 2021 and is 1,269 bytes in size.

TECHNICAL FIELD

The present invention relates to a paper-based, nucleic acid-detecting kit for detecting a nucleic acid, and more particularly, it is possible to easily and simply visualize the presence or absence of a target nucleic acid in a PCR amplicon of the present invention.

This application claims priority to and the benefit of Korean Patent Application No. 10-2018-0089182 filed in the Korean Intellectual Property Office on Jul. 31, 2018, and all the contents disclosed in the specification and drawings of that application are incorporated in this application.

BACKGROUND ART

Recently, polymerase chain reaction (PCR) and real-time PCR techniques, which can rapidly and simply amplify DNA fragments of a specific base sequence, have become common, so that it is easily detected and diagnosed whether a person is infected. A PCR technique is a technology capable of detecting the presence or absence of a target pathogen by adding a nucleic acid fragment sequence (primer) that specifically binds to a nucleic acid base sequence of the target pathogen and repeating the denaturation, annealing and polymerization processes according to the temperature to amplify a trace amount of the pathogen nucleic acid, and is a representative technology used for diagnosis.

The PCR technique enables an objective large-scale examination, unlike the cytologic examination of the Pap smear test, in the practical aspect of clinical diagnosis, and has been confirmed to have relative advantages in terms of test costs, experimental procedure, detection sensitivity, specificity, and the like, compared to cell tests or liquid hybrid capture based on the principle of measurement. However, since care is taken to design the PCR technique and interpret the results, there are disadvantages in that a highly skilled operator is required, it is required to go through a troublesome process to detect an amplicon of the PCR, and a PCR device can be used only in limited places due to its high price. Practically, when an infectious disease outbreak occurs, the disease needs to be promptly controlled, so that disease diagnosis should be a method that is quick, simple, inexpensive, and suitable for a point-of-care testing (POCT) environment regardless of location.

In order to satisfy the above-described needs, microfluidic engineering, microelectronics, optical systems and chip-based detection technologies have been developed, but most of these technologies have disadvantages in that complex manufacturing processes are still essentially required and these technologies can be used only in limited places satisfying conditions such as analysis devices.

As an example, a centrifugation-based separation-type visual detection system (SPIN-DNA) has been developed as a method for detecting human papillomavirus (HPV) DNA, but there is a problem in that the SPIN-DNA essentially includes a centrifugal device in order to separate a bead to which DNA is bound from other beads.

Therefore, there is a need for the development of molecular point-of-care testing (molecular POCT). In order to develop a diagnostic technique that can be applied to molecular point-of-care testing (molecular POCT), first of all, since a result should be quickly obtained by immediately detecting the DNA and RNA of a pathogen on site or analyzing the DNA and RNA of a cell in order to enable an immediate response to the disease, the DNA and RNA of the pathogen should be detected visually or with the naked eye without separate measuring equipment or knowledge, results should be obtained in a short time of less than 30 minutes, additional process steps such as a washing step should be eliminated, and inexpensive, accurate, and as excellent reproducibility is required without a measuring device or measuring instrument, a DNA diagnostic method finding strategy that has been conventionally used has a limitation.

The present inventors have made an effort to solve the above-described problems and develop a diagnostic method for molecular point-of-care testing (POCT), thereby leading to the development of a new DNA detection system which does not need a culturing or diluting step.

The items described as the aforementioned background art are only for the purpose of improving the understanding of the background of the present invention, and should not be taken as acknowledging that they correspond to the related art already known to those skilled in the art.

DISCLOSURE

Technical Problem

The present inventors have made intensive efforts to perform PCR on a specific gene and to find a device and a method which are capable of easily and simply detecting an amplicon thereof with the naked eye without a separate device. As a result, the present inventors devised a sensor structure including negatively-charged porous multilayer substrate and capture nanoparticles subjected to coating treatment with any one selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer, and confirmed the results of actually applying an amplicon of a sample that was subjected to PCR using a primer with a specific sequence using the same to a sensor and a kit of the present invention, thereby completing the present invention.

Therefore, an object of the present invention is to provide a paper-based, nucleic acid-detecting sensor consisting of: a negatively-charged porous first paper substrate; a separation layer stacked on one surface of the first paper substrate and including any one of Sepharose™ beads, glass beads and a mixture thereof; and a negatively-charged porous second paper substrate stacked on one surface of the separation layer.

Another object of the present invention is to provide a paper-based, nucleic acid-detecting kit including: a) a first solution in which capture nanoparticles subjected to coating treatment with any one selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer are dispersed; and b) the paper-based, nucleic acid-detecting sensor.

Still another object of the present invention is to provide a method for analyzing a PCR amplicon, the method including: (a) obtaining a reaction product by mixing the first solution of the paper-based, nucleic acid-detecting kit with a PCR amplicon labeled with any one selected from the group consisting of avidin, biotin, avidin-biotin, an antigen, a target molecule, and an oligonucleotide; and (b) adding the reaction product dropwise to a sensor of the paper-based, nucleic acid-detecting kit.

The other objects and advantages of the present invention will be more apparent from the following detailed description, claims and drawings of the invention.

Technical Solution

Hereinafter, preferred examples will be described in detail with reference to the accompanying drawings, such that a person skilled in the art to which the present invention pertains can easily carry out the present invention with reference to the accompanying drawings. However, in describing the preferred examples of the present invention in detail, when it is determined that the detailed description of publicly known relevant functions or configurations may unnecessarily obscure the gist of the present invention, the detailed description thereof will be omitted. Further, throughout the drawings, the same reference numerals will be used for parts that having similar functions and actions.

In addition, throughout the specification, when one part is 'connected' to another part, this includes not only a case where they are 'directly connected to each other', but also a case where they are 'indirectly connected to each other' with another member therebetween. Furthermore, the term 'include' a certain constituent element means that unless otherwise particularly described, it does not exclude other elements, but may further include other elements.

An aspect of the present invention relates to a paper-based, nucleic acid-detecting sensor consisting of: a negatively-charged porous first paper substrate; a separation layer stacked on one surface of the first paper substrate and including any one of Sepharose™ beads, glass beads and a mixture thereof; and a negatively-charged porous second paper substrate stacked on one surface of the separation layer. The structure of the paper-based, nucleic acid-detecting sensor is illustrated in FIG. 1.

As used herein, "nucleic acid" refers to a polymer of nucleotides with any length, and includes DNA or RNA.

Referring to FIG. 1, a paper-based, nucleic acid-detecting sensor 100 consists of a first paper substrate 110, a separation layer 120, and a second paper substrate 130, the first paper substrate 110 is disposed at the bottom, the separation layer 120 is formed on one surface of the first paper substrate 110, and the second paper substrate 130 is stacked on the entire surface of the separation layer 120.

The first paper substrate 110 and the second paper substrate 130 are porous and negatively-charged, and the pore sizes thereof may be the same or different from each other, but in consideration of the mobility of a mixture of a PCR amplicon and magnetic beads in the first paper substrate 110 and the second paper substrate 130, it is preferred that the pore sizes in the first paper substrate and the second paper substrate are the same.

It is preferred that the pore sizes of the first paper substrate 110 and the second paper substrate 130 are selected within a size of 1 to 5 μm.

The first paper substrate 110 and the second paper substrate 130 may be made of the same or different materials from each other, and the materials are not particularly limited as long as they are each independently paper-based, but may be any one selected from the group consisting of nitrocelluose, glass fiber Millipore® G041 sheet, Millipore® GFDX sheet, cellulosic Millipore® C083 sheet, Millipore® C048 sheet, Millipore® C068 fiber pad, Millipore® C083 sheet, Millipore® C248 pad, Healthcare CF1, CF3, CF4 cotton linter, Whatman Fusion 5™ paper, Std 14, and Std 15.

It is preferred that the total area of the second paper substrate is two to five times smaller than that of the first paper substrate, a reaction product of a PCR amplicon and magnetic beads is added dropwise onto the second paper substrate, the dropwise-added reaction product moves through the second paper substrate, the separation layer, and the first paper substrate in this order and spreads on the first paper substrate, and thus, can be identified with the naked eye, so that it is preferred that the total area of the second paper substrate is two to ten times smaller than that of the first paper substrate. If the total area of the second paper substrate is the same as or more than 10 times smaller the total area of the first paper substrate, and thus becomes smaller, there is a problem in that it becomes impossible to effectively detect whether or not a target nucleic acid is present in a PCR amplicon.

The thickness of the separation layer 120 is not particularly limited, but is preferably 10 to 100 μm in consideration of detection accuracy.

The separation layer 120 is a layer in which each of the dropwise-added PCR amplicon and a solution of nanoparticles are separated while the dropwise-added PCR amplicon and a solution of nanoparticles (capture nanoparticles subjected to coating treatment with any one selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer) move at different speeds according to whether a complex is formed or not.

Specifically, when a target nucleic acid is present in the PCR amplicon, the target nucleic acid will be present in a state of being labeled with any one of avidin, biotin, avidin-biotin, an antigen, a target molecule, and an oligonucleotide through the PCR process (varies depending on the primer set used for PCR). For example, in the case of a PCR product amplified with a biotin-labeled primer set, the biotin-labeled primer was used so that the formed target nucleic acid is in a state of being labeled with biotin. Therefore, in this case, it is preferred to use nanoparticles coated with streptavidin capable of reacting with biotin to form a complex.

When the complex formed as described above is loaded into the sensor, the complex passes through the separation layer of the sensor without staying in the separation layer, whereas when nanoparticles and a non-target nucleic acid are each present without forming a complex, the nanoparticles and the non-target nucleic acid cannot pass through the separation layer 120 and stay there, and thus do not spread to the first paper substrate.

In the experimental example of the present invention, a complex formed by the interaction between biotin and streptavidin was used by mixing the biotin-labeled target nucleic acid with magnetic beads (coated with streptavidin), and when the target nucleic acid was present and thus a complex was formed, the complex passed through the separation layer, and thus widely spread. In contrast, when the target nucleic acid is not present in the sample, the target nucleic acid is not amplified by the biotin-labeled primer in the PCR process and thus, the biotin-labeled nucleic acid is not present in the amplicon, so that the target nucleic acid and magnetic beads are each present without forming a complex with the nanoparticles coated with streptavidin, and fail to pass through the separation layer and stay there, and thus are present in a narrow circle.

The separation layer 120 is generated in the adsorption process by the charge and porosity when the complex is formed rather than by the density difference between Sepharose™ beads and glass beads and when the complex is not formed. When the complex is not formed, Sepharose™ beads and the glass beads cannot pass through the separation layer, and remain and stay in the separation layer, but when the complex is formed, Sepharose™ beads and the glass beads are less affected by adsorption due to charge and pores, so that the complex passes through the separation layer.

It is preferred that the separation layer 120 includes any one selected from Sepharose™ beads, glass beads, and a mixture thereof, and when the Sepharose™ beads and glass beads are simultaneously used, the separation layer 120 may be produced in a single layer by applying the mixed mixture, and may also be produced in the form of a multi-layer formed by separating Sepharose™ beads and glass beads from each other.

Another aspect of the present invention relates to a paper-based, nucleic acid-detecting kit including: a) a first solution in which capture nanoparticles subjected to coating treatment with any one selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer are dispersed; and b) the paper-based, nucleic acid-detecting sensor.

The paper-based, nucleic acid-detecting sensor may consist of: a negatively-charged porous first paper substrate; a separation layer stacked on one surface of the first paper substrate and including any one of Sepharose™ beads, glass beads and a mixture thereof; and a negatively-charged porous second paper substrate stacked on one surface of the separation layer.

The kit may further include a-1) a primer set that specifically binds to a target nucleic acid to be detected. The primer set may include a forward primer labeled with any one selected from the group consisting of avidin, biotin, avidin-biotin, an antigen, a target molecule, and an oligonucleotide, and a reverse primer labeled with any one selected from the group consisting of Cy3, Cy5, TAMRA, TEX, TYE, HEX, FAM, TET, JOE, MAX, ROX, VIC, Cy3.5, Texas Red® fluorophore, Cy5.5, TYE, BHQ, Iowa Black® RQ fluorophore, and IRDye.

As used herein, the primer refers to an oligonucleotide, and may act as a starting point for synthesis under conditions that induce the synthesis of a primer extension product that is complementary to a nucleic acid chain (template), that is, conditions of the presence of a polymer such as a nucleotide and a DNA polymerase, and suitable temperature and pH. The primer is a deoxyribonucleotide, and is a single chain. The primers used in the present invention may include naturally occurring dNMPs (that is, dANP, dGMP, dCMP, and dTMP), modified nucleotides, or non-naturally occurring nucleotides. Furthermore, the primer may also include a ribonucleotide. The primer should have a length large enough to prime the synthesis of an extension product in the presence of a polymer. The length of the primer is determined depending on the temperature, the field of application and the source of the primer, but is generally 10 to 150 nucleotides. A short primer molecule requires a low temperature to form a sufficiently stable hybrid complex with a template.

As used herein, the annealing or priming means that an oligodeoxynucleotide or nucleic acid is in apposition with a template nucleic acid, and the apposition forms a nucleic acid molecule complementary to the template nucleic acid or a portion thereof by allowing the polymerase to polymerize nucleotides.

In the paper-based, nucleic acid-detecting kit of the present invention, a sample is not particularly limited as long as the sample is a biological sample that can be separated from a specimen to be tested, but preferably, it is possible to use any sample that may include a target nucleic acid such as a cell, a tissue (biopsy sample, and the like), whole blood, serum, cerebrospinal fluid, semen, saliva, sputum, urine, stool, hair and a cell culture fluid without limitation. For better understanding, as an example, HPV16 DNA was tested as a target sample. That is, HPV16 DNA was used as a template for synthesis, and a PCR amplicon was obtained by adding the primer set to perform PCR. In the PCR amplicon, the target nucleic acid was labeled with any one selected from the group consisting of avidin, biotin, avidin-biotin, an antigen, a target molecule, and an oligonucleotide, and the repeat number was in a range of 1 to 10. The labeled nucleic acid molecule is visualized by the nucleic acid-detecting kit of the present invention so as to be later distinguished as negative or positive with the naked eye.

Upon contact with the target nucleic acid in the sample separated from the specimen to be tested, the primer set is hybridized, and is subjected to amplification of the target nucleic acid by extending a hybrid product.

In this case, due to a forward primer labeled with any one selected from the group consisting of avidin, biotin, avidin-biotin, an antigen, a target molecule, and an oligonucleotide in the primer set, the target nucleic acid is formed by being labeled with any one selected from the group consisting of avidin, biotin, avidin-biotin, an antigen, a target molecule, and an oligonucleotide. Preferably, it is preferred that the forward primer is labeled with avidin, biotin, or avidin-biotin, and through this, it is preferred that the target nucleic acid is formed by being labeled with avidin, biotin, or avidin-biotin.

The primer set may further include other suitable buffers, enzymes such as deoxyribonucleotides, Taq-polymerase and reverse transcriptase, DNase, RNase inhibitors, DEPC-water, sterile water, or the like, as needed.

The amplification is a polymerase chain reaction (PCR), and in the present invention, PCR is a method of amplifying a target nucleic acid from a primer pair that specifically binds to the target nucleic acid using a polymerase, and may include a thermal cycle for hybridization and denaturation. Such PCR methods include single PCR that amplifies only one target at a time and multiplex PCR that amplifies multiple targets at a time, and a plurality of primer sets can be used in the multiplex PCR.

That is, the primer set may include a single primer set or a plurality of primer sets.

The reverse primer may also be labeled with fluorescence. The fluorescence may be any one selected from the group consisting of Cy3, Cy5, TAMRA, TEX, TYE, HEX, FAM, TET, JOE, MAX, ROX, VIC, Cy3.5, Texas Red® fluorophore, Cy5.5, TYE, BHQ, Iowa Black® RQ fluorophore, and IRDye. In the case where the reverse primer is labeled with fluorescence, when the PCR amplicon is loaded onto the paper-based, nucleic acid-detecting kit, the moved position can be confirmed by fluorescence, and it can be confirmed whether or not the target nucleic acid is present in the PCR amplicon by confirming the moved position by fluorescence.

The nanoparticle of the present invention may be any one selected from the group consisting of a magnetic bead, a gold (Au) nanoparticle, a silver (Ag) nanoparticle, a platinum (Pt) nanoparticle, a quantum dot, an upconversion nanoparticle (UCNP) graphene-nanoparticle complex, a color dyed particle, and a latex nanoparticle. The nanoparticles may be subjected to coating treatment with any one which is capable of capturing a target nucleic acid amplified by a primer in an amplicon, and forming a complex by seizing, selected from the group consisting of avidin, streptavidin, an antibody capable of being bound to an antigen bound to the primer by an antigen-antibody reaction, an aptamer that specifically binds to a target molecule bound to the primer and an oligonucleotide complementary to an oligonucleotide bound to the primer.

Specifically, since an amplicon amplifying a desired nucleic acid is amplified using a primer set labeled with any one selected from the group consisting of avidin, biotin, avidin-biotin, an antigen, a target molecule, and an oligonucleotide, the amplicon includes a target nucleic acid labeled with any one selected from the group consisting of avidin, biotin, avidin-biotin, an antigen, a target molecule, and an oligonucleotide.

Here, depending on the type of labeled nucleic acid, when nanoparticles coated with any one selected among avidin, streptavidin, an antibody capable of being bound to an antigen bound to the primer by an antigen-antibody reaction, an aptamer that specifically binds to a target molecule bound to the primer and an oligonucleotide complementary to an oligonucleotide bound to the primer are selected such that a complex is formed by specifically binding to the target nucleic acid, and then the amplicon and the first solution are reacted, nanoparticles may capture the target nucleic acid via 'biotin-streptavidin', 'antigen-antibody', 'target molecule-aptamer', and 'oligonucleotide-oligonucleotide (complementary bond)' reactions (complex formation).

It is preferred that the nanoparticles are streptavidin-coated magnetic beads, this is because the streptavidin-coated magnetic beads efficiently serve to selectively separate the target nucleic acid from the PCR amplicon by seizing and capturing a target nucleic acid labeled with biotin to form a complex. In the present invention, Dynabeads® MyOne Streptavidin C1 magnetic beads (size: 1 µm, capacity 80 µg) coated with the streptavidin were used.

Since the present invention does not adopt the detection using the density of the complex as a principle, the present invention is not affected by the size of the complex, so that the size of the magnetic beads is not particularly limited, but is preferably 0.1 to 1 µm.

Since the paper-based, nucleic acid-detecting sensor has been described above in detail, the repeated contents thereof will be omitted.

Still another aspect of the present invention relates to a method for analyzing a PCR amplicon, the method including: (a) obtaining a reaction product by mixing the first solution of the paper-based nucleic acid-detecting kit with a PCR amplicon labeled with any one selected from the group consisting of avidin, biotin, avidin-biotin, an antigen, a target molecule, and an oligonucleotide; and (b) adding the reaction product dropwise to a sensor of the paper-based, nucleic acid-detecting kit.

The principle of the paper-based, nucleic acid-detecting kit of the present invention is schematically illustrated in FIG. 2, and will be specifically described below with reference to the drawing.

(a) A reaction product is obtained by mixing the first solution of the paper-based, nucleic acid-detecting kit with a PCR amplicon labeled with any one selected from the group consisting of avidin, biotin, avidin-biotin, an antigen, a target molecule, and an oligonucleotide. Specifically, a first solution, in which capture nanoparticles subjected to coating treatment with any one selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer are dispersed, is added to a PCR amplicon to be checked for the presence of a target nucleic acid.

If a target nucleic acid labeled with any one selected from the group consisting of avidin, biotin, avidin-biotin, an antigen, a target molecule, and an oligonucleotide is present in the PCR amplicon, any one selected from the group consisting of avidin, biotin, avidin-biotin, an antigen, a target molecule, and an oligonucleotide of the target nucleic acid forms a bond with any one among avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer to produce a complex.

As an example, when the target nucleic acid is labeled with biotin, as the nanoparticles of the first solution, streptavidin-coated nanoparticles (preferably magnetic particles) are used, and the biotin-labeled target nucleic acid and the streptavidin-coated nanoparticles form a complex through strong hydrophobic bonds. In contrast, when the biotin-labeled target nucleic acid is not present in the PCR amplicon, the nanoparticles of the first solution do not form a complex with the target nucleic acid and are present in the solution as they are.

Step (a) can be fully achieved by simple mixing and is not restricted by time and place. Further, since a step of removing the unreacted magnetic beads or nucleic acid needs not be separately introduced, Step (a) is much simpler and faster than the process of detecting a PCR amplicon in the related art, and thus can be usefully performed anywhere.

An amplicon (amplicon DNA) labeled with any one selected from the group consisting of avidin, biotin, avidin-biotin, an antigen, a target molecule and an oligonucleotide in Step a) may be obtained by including: a-1) extracting a nucleic acid from a biological sample separated from a specimen to be tested; and a-2) obtaining a PCR amplicon, in which a desired nucleic acid is amplified, by treating the primer set including a forward primer labeled with any one selected from the group consisting of avidin, biotin, avidin-biotin, an antigen, a target molecule, and an oligonucleotide and a reverse primer (fluorescence-labeled reverse primer).

A sample is not particularly limited as long as the sample is a biological sample that can be separated from a specimen to be tested, but preferably, it is possible to use any sample that may include a target nucleic acid such as a cell, a tissue (biopsy sample, and the like), whole blood, serum, cerebrospinal fluid, semen, saliva, sputum, urine, stool, hair and a cell culture fluid without limitation. For better understanding, as an example, HPV16 DNA was tested as a target sample. That is, HPV16 DNA was used as a template for synthesis, and a PCR amplicon was obtained by adding the primer set to perform PCR. In the PCR amplicon, the target nucleic acid was labeled with any one selected from the group consisting of avidin, biotin, avidin-biotin, an antigen, a target molecule, and an oligonucleotide, and the repeat number was in a range of 1 to 10. A nucleic acid molecule labeled with any one selected from the group consisting of avidin, biotin, avidin-biotin, an antigen, a target molecule, and an oligonucleotide is visualized so as to be later distinguished as negative or positive with the naked eye by the nucleic acid-detecting kit of the present invention. It is preferred that the target nucleic acid in the PCR amplicon is labeled with biotin.

The nucleic acid of the present invention includes DNA and RNA, and the amplification of DNA is not particularly limited as long as the amplification is a conventionally known amplification method (including isothermal amplification), but may be preferably PCR. Further, any method conventionally known in the amplification of RNA can be used without particular limitation, and the amplification may be preferably a method of synthesizing RNA and then amplifying RNA, and more preferably RT-PCR.

The polymerase chain reaction (PCR) is a method of amplifying a target nucleic acid from a primer pair that specifically binds to the target nucleic acid using a polymerase, and may include a thermal cycle for hybridization and denaturation. Such PCR method includes single PCR that amplifies only one target at a time and multiplex PCR that amplifies multiple targets at a time, and a plurality of primer sets can be used in the multiplex PCR.

That is, the primer set may include a single primer set or a plurality of primer sets.

The primer set may include a primer pair represented by SEQ ID NOS: 1 and 2, and may include a primer pair represented by SEQ ID NOS: 3 and 4.

The primer set may further include other suitable buffers, enzymes such as deoxyribonucleotides, Taq-polymerase and reverse transcriptase, DNase, RNase inhibitors, DEPC-water, sterile water, or the like, as needed.

Next, (b) the reaction product is added dropwise to the sensor of the paper-based, nucleic acid-detecting kit. There are problems in that the reaction product should be added dropwise onto the second paper substrate of the paper-based, nucleic acid-detecting kit, and when the reaction product is added dropwise to other places, the PCR amplicon is not sufficiently separated, and thus accuracy is reduced.

After Step (b), it is possible to further include (c) determining whether or not the target nucleic acid is included in the PCR amplicon through the range of the reaction product spread on the surface of the first paper substrate of the sensor.

Specifically, when the reaction product of the PCR amplicon and the magnetic beads is added dropwise onto the second paper substrate 130 of the paper-based, nucleic acid-detecting kit 100, the dropwise added reaction product moves through the second paper substrate 130, the separation layer 120, and the first paper substrate 110 in this order and spreads on the first paper substrate 110, and thus, can be identified with the naked eye. If a target nucleic acid-magnetic bead complex is present in the reaction product, the target nucleic acid-magnetic bead complex will spread over the entire substrate as the target nucleic acid-magnetic bead complex is clearly distinguished by a separation layer including Sepharose™ beads and glass beads. In this case, a brown color is confirmed with the naked eye. In contrast, when the complex is not present in the reaction product and the nanoparticles (preferably magnetic beads) are present as they are, the complex cannot spread on the first substrate through the separation layer, and stays in the second paper substrate 130 and the separation layer 120. Due to the difference in visual results in such a sensor, it is possible to effectively and reproducibly confirm whether or not the target nucleic acid is present in the PCR amplicon.

As described above, the paper-based, nucleic acid-detecting sensor, kit and detection method developed in the present invention have various advantages in visualizing the presence or absence of the target nucleic acid present in the PCR amplicon. 1) Unlike the related art, the paper-based, nucleic acid-detecting sensor, kit and detection method developed in the present invention do not require a long culture time or washing step because they require only one mixing step and a series of steps of adding a reaction product dropwise onto the sensor, so that the procedure can be simplified. 2) Since an external force is not used in the detection process in the present invention, the present invention does not require an external device, and thus not restricted by location. In contrast, the related art generally has complicated structural problems, in that a driving force for the capillary phenomenon is required, an external device is indispensable, and an absorption pad should be always provided.

As an example, the lateral flow immunochromatographic assay (LFIA) is the easiest and most successful tool available in a situation where financial resources are limited because only a process of adding a specimen to be tested initiates a series of reactions required to obtain readable results later. Specifically, in the LFIA, in a classic sandwich format, the specimen to be tested moves while dissolving a labeled antibody, and when the specimen and the antibody are chromatographed together along a reaction membrane, and thus bound to a capture region, an accumulation that can be observed with the naked eye is formed only when a labeling material is captured. However, the detection limit of LFIA is clearly different depending on the type of labeling material, and there are disadvantages in that not only is there an interference phenomenon due to various factors such as maternally-derived antigens, but also an elaborate design of antibodies and detection probes for capturing a specimen to be tested is required, and the production process is difficult. Furthermore, there is a limitation in that it is very difficult to detect only a target nucleic acid in the PCR amplicon through the LFIA.

Meanwhile, in the case of a technique in the related art, such as the SPIN-DNA system, nanoparticles are affected by various factors such as the concentration of Sepharose™ beads, the density of Sepharose™ beads, the intercalation of a dye [GelRed™ (trade name)], centrifugal force, and the presence or absence of fluorescence-labeling of PCR amplicon, and temperature, which means that the related art such as the SPIN-DNA system is affected by various factors, indicating that reproducibility or accuracy may vary depending on the place and time, and there are restrictions on the place or conditions.

However, in the case of a paper-based, on-site diagnostic kit of the present invention, it was confirmed that the mobility of nanoparticles (preferably magnetic bids) was not changed by the various factors previously described (the concentration of Sepharose™ beads, the intercalation of a dye [GelRed™ (trade name)], centrifugal force, and the presence or absence of fluorescence-labeling of PCR amplicon, and the like). Furthermore, when the PCR amplicon with and without the introduction of a fluorescent labeling material was loaded into the paper-based, on-site diagnostic kit of the present invention, the results were the same (not shown). Further, unlike the related art, the paper-based, on-site, diagnostic kit of the present invention does not require centrifugation or the addition of GelRed™, and thus has an advantage in that the detection step can be omitted.

In the paper-based, on-site diagnostic kit of the present invention, a moving pattern of nanoparticles (preferably magnetic beads) when a PCR amplicon with a target nucleic acid is loaded and a moving pattern of nanoparticles (preferably magnetic beads) when a PCR amplicon without a target nucleic acid is loaded are completely different, so that even though the results are affected by the concentration of Sepharose™ beads, the degree is insignificant, and the results do not lead to a problem in that the results are not overturned or accuracy or reproducibility is reduced. In addition, the paper-based, on-site diagnostic kit of the present invention has an advantage in that the kit is not affected by the size of the target nucleic acid or the size of the PCR amplicon.

Therefore, the present invention not only solves the problems of the above-described related art, but also omits additional devices, is structurally further simplified, and can visualize whether or not the target nucleic acid is present in the PCR amplicon, so that the PCR amplicon can be detected anywhere.

The paper-based, nucleic acid-detecting kit according to the present invention has an advantage in that the kit can be widely applied regardless of the type of nucleic acid when a biotinylated PCR amplicon is produced by performing general PCR. That is, since the paper-based, nucleic acid-detecting sensor and kit and detection method of the present invention are suitable for the POCT (point-of-care testing) environment, they can be widely used in the field of POCT diagnosis in patient diagnosis and treatment.

With respect to the terms used in the present invention, general terms currently and widely used are selected in consideration of function in the present invention, but the terms may vary according to an intention or precedent of a technician practicing in the art, an advent of a new technology, and the like. Further, in specific cases, there is also a term arbitrarily chosen by the applicant, and in this case, the meanings thereof will be described in detail in the corresponding part of the Detailed Description of the present invention. Accordingly, the term used in the present invention should not be defined merely as a simple name of the term, but should be defined based on the meaning of the term and overall content of the present invention.

Terms such as first and second may be used to explain various constituent elements, but the constituent elements are not limited by the terms. The terms are used only to distinguish one constituent element from another constituent element. For example, without departing from the scope of the invention, a first constituent element may be called a second constituent element, and similarly, the second constituent element may be called the first constituent element. The term and/or includes a combination of a plurality of related described items, or any item among the plurality of related described items.

Throughout the specification of the present invention, when one part "includes" one constituent element, unless otherwise specifically described, this does not mean that another constituent element is excluded, but means that another constituent element may be further included. Throughout the specification of the present invention, a term of a degree, such as "about" or "substantially", is used as meaning a corresponding numerical value or used as a meaning close to the numerical value when a natural manufacturing and a material tolerance error are presented in a described meaning, and is used to prevent an unconscientious infringer from illegally using disclosed contents including a numerical value illustrated as being accurate or absolute in order to help understanding of the present invention.

Throughout the specification of the present invention, the term "combination thereof" included in the Markush type expression means a mixture or combination of one or more selected from the group consisting of constituent elements described in the Markush type expression, and means including one or more selected from the group consisting of the above-described constituent elements.

Advantageous Effects

The features and advantages of the present invention are summarized as follows:

i. The present invention provides a paper-based, nucleic acid-detecting sensor capable of easily and simply detecting the presence of a target nucleic acid in a PCR amplicon.

ii. In addition, the present invention provides a paper-based, nucleic acid-detecting kit capable of easily and simply detecting the presence of a target nucleic acid in a PCR amplicon and a nucleic acid detecting method using the same.

iii. The present invention can easily and simply detect whether or not a target nucleic acid is present in a PCR amplicon by binding a target nucleic acid labeled with any one of avidin, biotin, avidin-biotin, an antigen, a target molecule, and an oligonucleotide to capture nanoparticles subjected to coating treatment with any one selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer to form a complex, allowing the complex to be separated and move along the structure of a sensor when the complex is added dropwise onto the sensor, and using a function in which the separation and moving aspects are finally visualized the outside of the sensor.

MODES OF THE INVENTION

Figure 1:
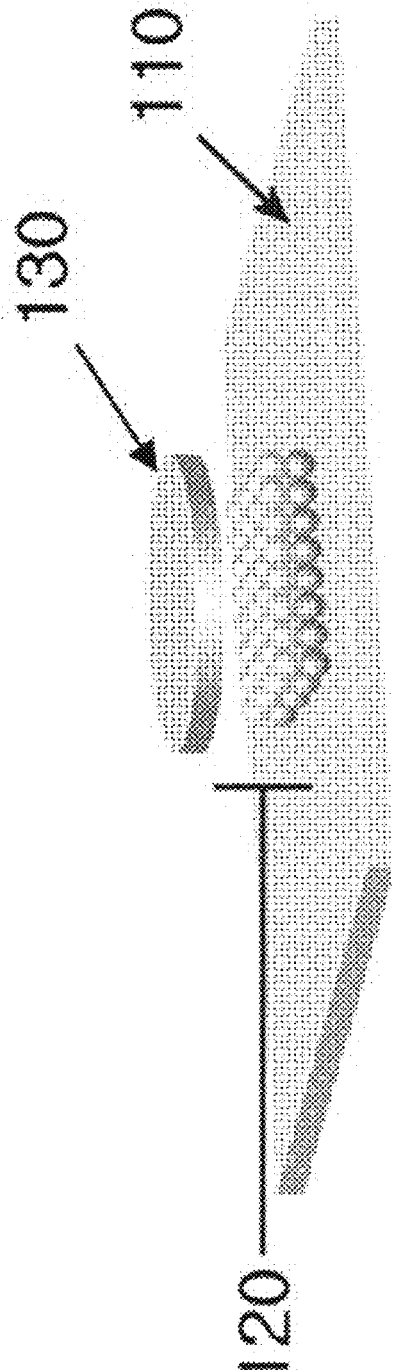
FIG. 1 is a perspective view illustrating a structure of a paper-based, nucleic acid-detecting sensor of the present invention.
Figure 2:
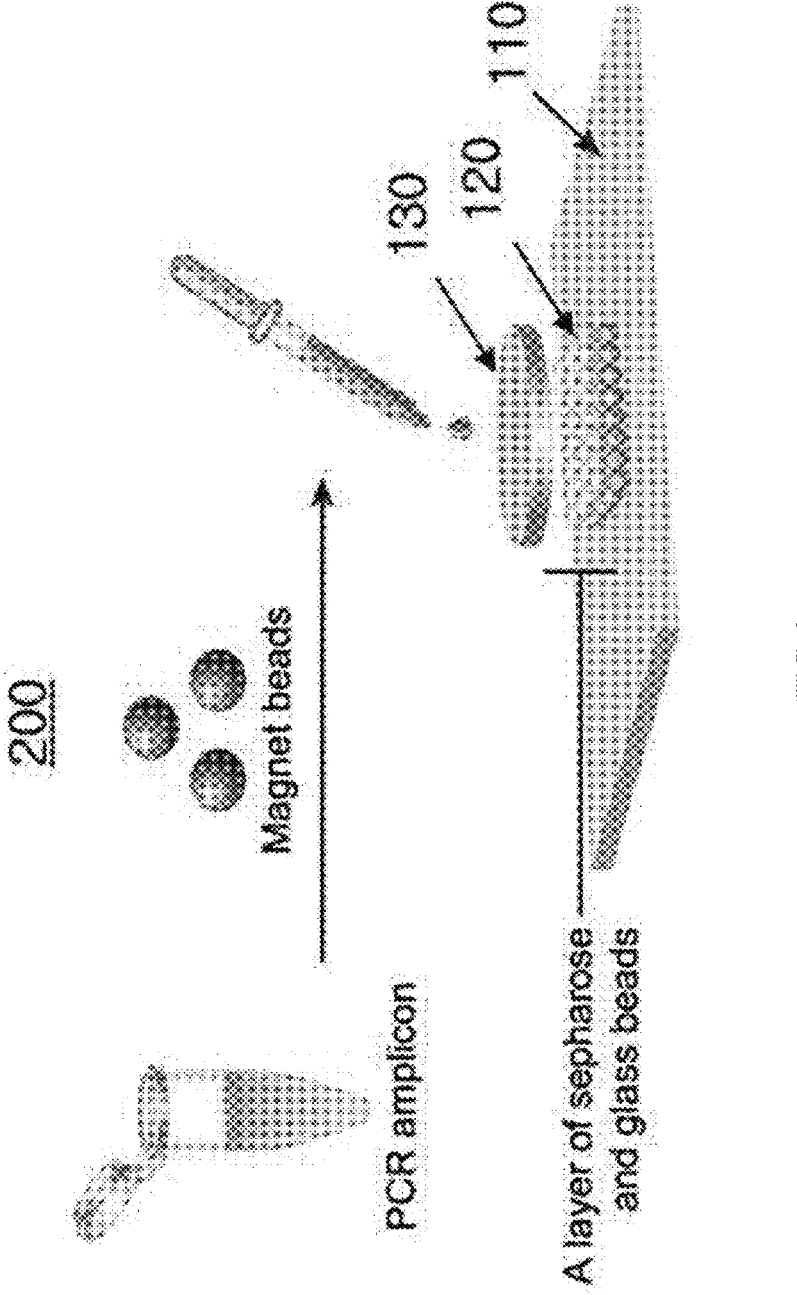
FIG. 2 is a view schematically illustrating the principle of a paper-based, nucleic acid-detecting kit of the present invention.

Hereinafter, the present invention will be described in more detail through Examples. These Examples are provided only for more specifically describing the present invention, and it will be obvious to a person with ordinary skill in the art to which the present invention pertains that the scope of the present invention is not limited by these Examples according to the gist of the present invention.

EXAMPLES

<Example 1> Preparation of PCR Amplicon

1) Preparation of Sample

As an example, the reproducibility and accuracy of the present invention was intended to be confirmed by detecting DNA in an HPV subject using a paper-based DNA diagnostic kit of the present invention. A sample to be used with the paper-based DNA diagnostic kit of the present invention is not particularly limited as long as the sample is a biotin-labeled amplicon obtained by general PCR amplification, and the sample in the present invention was prepared as follows.

When genomic DNA was extracted from a cervical specimen to be tested, a nucleic acid was extracted according to the manufacturer's instructions using a nucleic acid extraction kit (QIAamp DNA Micro kit, QIAGEN, Valencia, CA, USA or ChargeSwitch gDNA 1 μl Serum Kit, Life Technologies, NY, USA), and 24 HPV16 DNA positive samples and 6 positive samples of different HPV types were prepared for repeated experiments by requesting a human papillomavirus (HPV) DNA standard for sale to the Ministry of Food and Drug Safety and the National Institute for Biological Standards and Control (NIBSC). A polymerase chain reaction was performed using a primer set including reverse and forward primers (the following Table 1) that specifically hybridize with the target nucleic acid, and amplicons of each sample were obtained. A primer set of the present invention was manufactured to enable not only PCR amplification but also isothermal amplification (preferably helicase dependent amplification (HDA), recombinase polymerase amplification (RPA)), and was modified with reference to conventionally known literature (Virol J. 2010 Aug. 19; 7:194).

TABLE 1

| Name of target nucleic acid | | Sequence of primers (5' -> 3') | Size of fragment (bp) | SEQ ID NO: |
|---|---|---|---|---|
| HPV 16 DNA | Forward primer | 5'-biotin-TTGTTGGGG TAACCAACTATTTGTTACT GTT | 136 | 2 |
| | Reverse primer | 5'-Cy3-CCTCCCCATGT CTGAGGTACTCCTTAAAG | | 2 |

TABLE 1-continued

| Name of target nucleic acid | | Sequence of primers (5' -> 3') | Size of fragment (bp) | SEQ ID NO: |
|---|---|---|---|---|
| HPV | Forward primer | 5'-biotin-TGTCAGAA CCATATGGCGACAGCTT | 95 | 3 |
| | Reverse primer | 5'-Cy3-TTCACCAACAG CACCAGCCCTATTA | | 4 |

As the reverse primer, a reverse primer, in which Cy3 was present or not present at the 5' end, was used, and as the forward primer, a forward primer that was labeled with biotin at the 5' end was used. This is for allowing the biotin to form an interaction with b) streptavidin-coated magnetic beads (Dynabead MyOne Streptavidin C1) in the present invention.

After 1 μl of the primer set (10 pmole/μl) was mixed with 5 μl of HotStarTaqplus Master Mix 10 μl, Template DNA (1 ng/μl) and 4 μl of distilled water, PCR was performed by maintaining 95° C. for 10 minutes and repeating one cycle [at 95° C. for 30 seconds, at 55° C. for 30 seconds, and at 72° C. for 30 seconds] 40 times as amplification conditions.

Through the above-described process, PCR analysis was performed on HPV16 and the other types of HPV, and 20 μl of a biotinylated amplicon (amplified DNA) was obtained. A portion of the biotin-labeled amplicon thus produced was used as a positive control by the Roche Cobas 4800 HPV test (Roche HPV; Roche Molecular Diagnostics, Pleasanton, CA, USA) and later compared with the analytical results of the present invention.

<Example 2> Confirmation of Analysis Results of Amplicon Using Paper-Based, Nucleic Acid-Detecting Kit 1) Paper-Based, Nucleic Acid-Detecting Kit A first solution (magnetic beads suspension) in which streptavidin-coated magnetic beads were dispersed (10 mg/ml Dynabead My One Streptavidin C1, Life Technologies, Grand Island, NY, USA) was prepared.

Further, a first paper substrate was prepared using Fusion 5 paper (GE Healthcare, Pittsburgh, PA, USA) with a size of 6×6 cm. A separation layer was formed by applying 24 μl of a Sepharose™ beads solution (a low ionic strength solution (LISS) buffer in which 2 mg/μl was dispersed) and 8 μl of 75 mm glass beads (1:1 v/v with LISS and 0.1% Triton-X) with a surface (circular shape) of 6×6 mm onto the first paper base, and drying the first paper substrate at room temperature. Next, a second paper substrate was manufactured by stacking Fusion 5 paper (GE Healthcare, Pittsburgh, PA, USA) with a size of 6×6 mm in a circular shape on the separation layer. The second paper substrate is stacked on the separation layer, but it is preferred that the second paper substrate is stacked so as to cover the entire surface of the separation layer. Through the above-described process, a paper-based, nucleic acid-detecting sensor having a structure of a first substrate/a separation layer/a second substrate was manufactured as illustrated in the following FIG. 1.

The Fusion 5 paper used for the first and second paper substrates is characterized by being porous, having an average particle retention size of 2.3 μm, and being negatively charged (—).

2) PCR Amplicon Analysis Using Paper-Based, Nucleic Acid-Detecting Kit

8 μl of the first solution (magnetic beads suspension) in which streptavidin-coated magnetic beads were dispersed (10 mg/ml Dynabead My One Streptavidin C1, Life Technologies, Grand Island, NY, USA) was mixed with a PCR amplicon (positive sample) of biotin-labeled HPV obtained from Example 1. As a control (negative sample) thereof, a PCR amplicon in which no target nucleic acid was present was used as a sample (negative).

The mixed solution was added dropwise onto the second paper substrate of the paper-based, nucleic acid-detecting sensor. After the mixed solution was added dropwise onto the paper-based, nucleic acid-detecting sensor, 60 μl of a low ionic strength solution (LISS) buffer (BLISS, Ortho-Clinical Diagnostics) was further added dropwise thereto. The mixed solution moves on the first paper substrate via a separation layer including Sepharose™ beads and 75-mm glass beads along the second paper substrate, depending on the mobility of a precipitate, and depending on the degree of movement of the precipitate, it becomes possible to determine whether a target nucleic acid is present (positive) or not (negative) in the PCR amplicon with the naked eye. Since the above-described process is performed within several to several tens of seconds, it took about 1 to 10 minutes to confirm the result with the naked eye.

Figure 3:
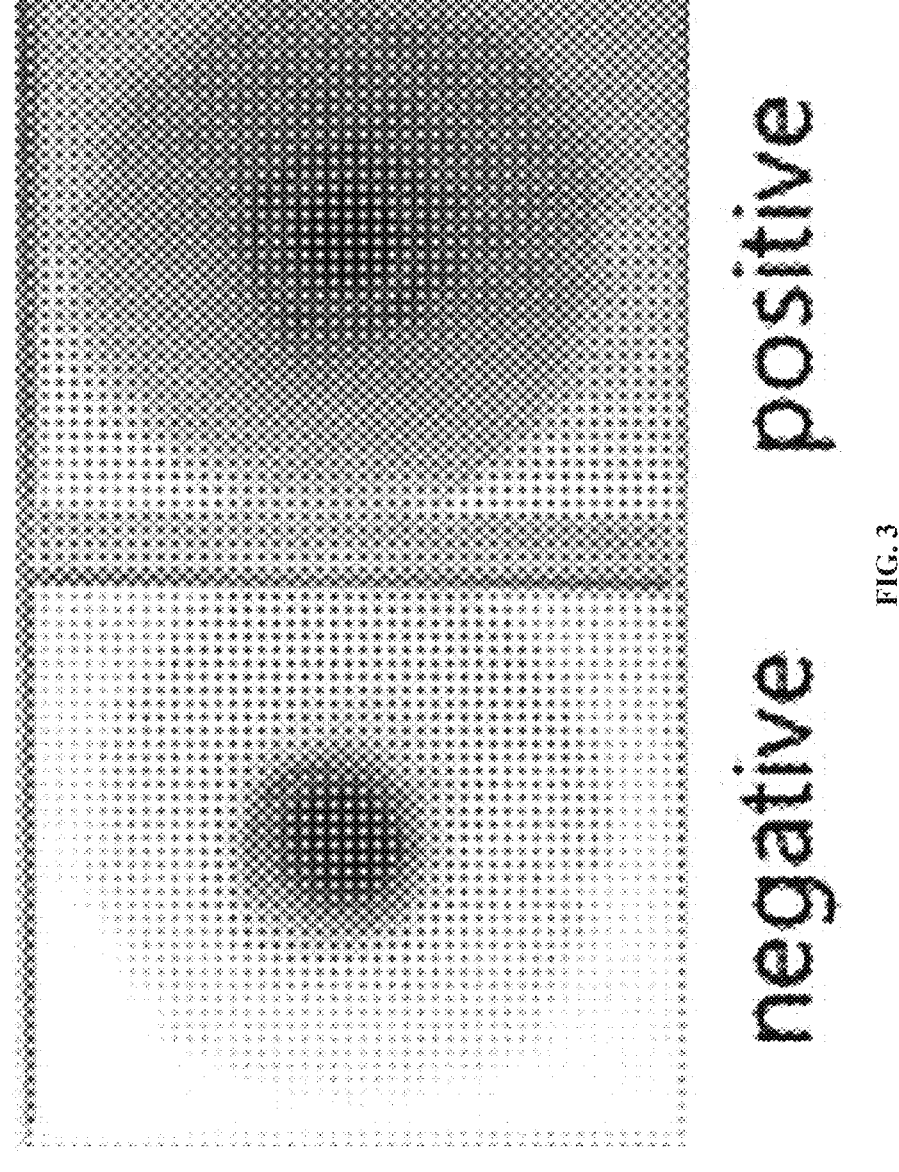
FIG. 3 illustrates the results of detecting a target nucleic acid through a paper-based, on-site diagnostic kit according to the present invention.

3) Comparison of Analysis Results when PCR Amplicon with or without Target Nucleic Acid is Mixed with the First Solution FIG. 3 relates to a result of detecting the target nucleic acid by the paper-based, on-site diagnostic kit according to the present invention, the right side indicates that a PCR amplicon of biotin-labeled HPV is used as a positive sample, and the left side indicates that a PCR amplicon of HPV not labeled with biotin is used as a negative sample.

As illustrated in FIG. 3, it was confirmed that there was a visually remarkable difference between a paper-based, on-site diagnostic kit (right side) loaded with a PCR amplicon in which the target nucleic acid was present and a paper-based, on-site diagnostic kit (left side) loaded with a PCR amplicon in which the target nucleic acid was not present. That is, when the PCR amplicon in which the target nucleic acid is present is loaded, the brown color of the magnetic beads widely spreads throughout the paper-based, on-site diagnostic kit, so that the presence of the target nucleic acid in the PCR amplification product can be easily determined with the naked eye.

Generally, in order to visually detect the presence or absence (positive/negative) of a target nucleic acid in a PCR amplicon, an external force such as electric power, motor driving or centrifugal force, or external detection equipment is indispensable. However, in the case of the paper-based, on-site diagnostic kit of the present invention, as illustrated in FIG. 3, the results are visually derived such that the presence of the target nucleic acid in the PCR amplicon can be determined with the naked eye without an external force or external detection equipment. This can be explained as follows.

When the PCR amplicon including the target nucleic acid is mixed with the first solution (magnetic beads) of the present invention, the biotin bound to the target nucleic acid and the streptavidin coated on the magnetic beads interact with each other to form a target nucleic acid-magnetic bead complex (amplicon-attached). In contrast, when a PCR amplicon including no target nucleic acid is mixed with the first solution (magnetic beads) of the present invention, the magnetic beads cannot form a complex and are still present as they are. Therefore, the target nucleic acid-magnetic bead complex and the magnetic beads have a difference in mobility, and as the difference in mobility is clearly distinguished by a separation layer including Sepharose™ beads and glass beads, the target nucleic acid-magnetic bead complex will spread throughout the entire substrate, and the magnetic beads remain on the initially added dropwise second substrate.

In other words, it can be seen that the paper-based, nucleic acid-detecting kit according to the present invention allows the presence or absence of a target nucleic acid to be reproducibly, accurately, easily, and simply determined with the naked eye from a PCR amplicon even when a probe for capturing or detecting the target nucleic acid in the PCR amplicon is not immobilized on a substrate (even when a separate configuration is not included on a substrate).

<Example 3> Confirmation of Analysis Results of Amplicon Using Paper-Based, Nucleic Acid-Detecting Kit 1) Paper-Based, Nucleic Acid-Detecting Kit A first solution (magnetic beads suspension) in which streptavidin-coated magnetic beads were dispersed (10 mg/ml Dynabead My One Streptavidin C1, Life Technologies, Grand Island, NY, USA) was prepared.

Further, a first paper substrate was prepared using Fusion 5 paper (GE Healthcare, Pittsburgh, PA, USA) with a size of 6×6 cm. A separation layer was formed by applying 24 μl of a Sepharose™ beads solution (a low ionic strength solution (LISS) buffer in which 2 mg/μl was dispersed) and 8 μl of 75 mm glass beads (1:1 v/v with LISS and 0.1% Triton-X) with a surface (circular shape) of 6×6 mm onto the first paper base, and drying the first paper substrate at room temperature. Next, a second paper substrate was manufactured by stacking Fusion 5 paper (GE Healthcare, Pittsburgh, PA, USA) with a size of 6×6 mm in a circular shape on the separation layer. The second paper substrate is stacked on the separation layer, but it is preferred that the second paper substrate is stacked so as to cover the entire surface of the separation layer. Through the above-described process, a paper-based, nucleic acid-detecting sensor having a structure of a first substrate/a separation layer/a second substrate was manufactured as illustrated in the following FIG. 1.

The Fusion 5 paper used for the first and second paper substrates is characterized by being porous, having an average particle retention size of 2.3 μm, and being negatively charged (−).

2) PCR Amplicon Analysis Using Paper-Based, Nucleic Acid-Detecting Kit

A biotin-labeled PCR amplicon was obtained for each in the same manner as in Example 1, except that human papillomavirus (HPV) DNA standards (NIBSC code: 06/202, HPV16DNA WHO standards) diluted 10, $10^2$, $10^3$, $10^4$, and $10^5$ times were used. As a control (negative sample) thereof, an amplicon was obtained by amplifying a sample (10, $10^2$, $10^3$, $10^4$, and $10^5$-fold diluted) in which no target nucleic acid was present by PCR.

8 μl of the first solution (magnetic beads suspension) in which streptavidin-coated magnetic beads were dispersed (10 mg/ml Dynabead My One Streptavidin C1, Life Technologies, Grand Island, NY, USA) was mixed with the biotin-labeled PCR amplicon (positive sample) obtained above.

The mixed solution was added dropwise onto the second paper substrate of the paper-based, nucleic acid-detecting sensor. After the mixed solution was added dropwise onto the paper-based, nucleic acid-detecting sensor, 60 μl of a low ionic strength solution (LISS) buffer (BLISS, Ortho-Clinical Diagnostics) was further added dropwise thereto. The mixed solution moves on the first paper substrate via a separation layer including Sepharose™ beads and 75-mm glass beads along the second paper substrate, depending on the mobility of a precipitate, and depending on the degree of movement of the precipitate, it becomes possible to determine whether a target nucleic acid is present (positive) or not (negative) in the PCR amplicon with the naked eye. Since the above-described process is performed within several to several tens of seconds, it took about 1 to 10 minutes to confirm the result with the naked eye.

3) Evaluation Analysis of Detection Sensitivity and Performance

Figure 4:
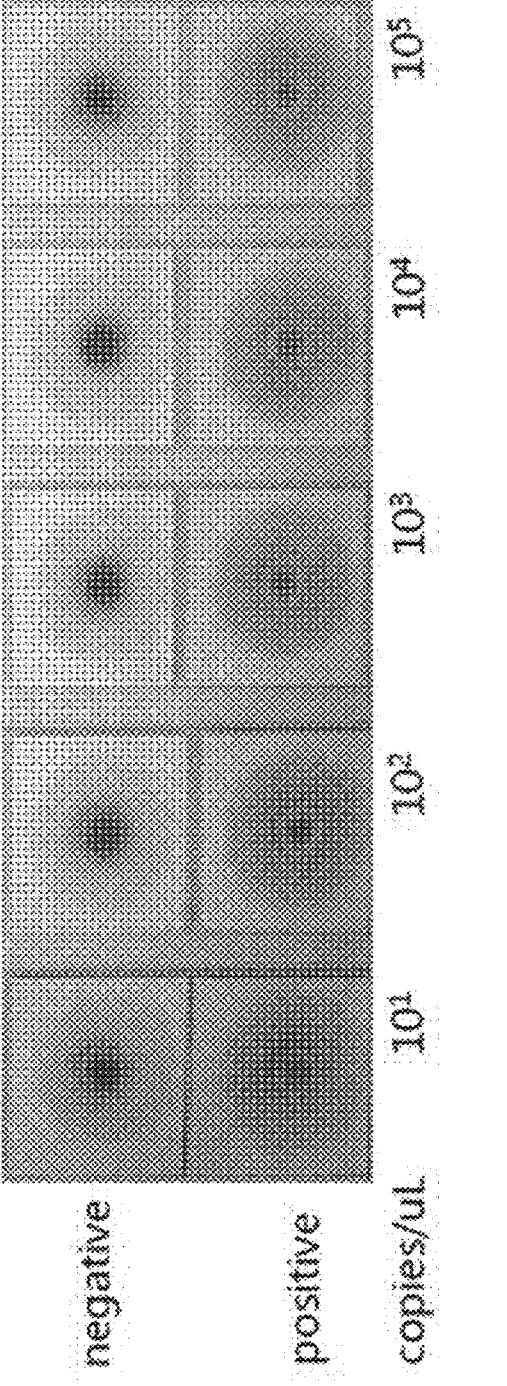
FIG. 4 illustrates the results of evaluating the detection sensitivity and performance of the paper-based, nucleic acid-detecting sensor of the present invention.

FIG. 4 illustrates the results of evaluating the detection sensitivity and performance of the paper-based, nucleic acid-detecting sensor of the present invention. As illustrated in FIG. 4, it can be seen that the paper-based, nucleic acid-detecting kit of the present invention exhibits excellent detection sensitivity even though a PCR amplicon is produced using a $10^5$-fold diluted biological sample. Further, it was reproducibly confirmed that the paper-based, nucleic acid-detecting kit of the present invention has a detection sensitivity of at least $10^1$ copies of HPV DNA/mL through the above-described experiments (12 replications for 6 days) (n=30). Since it was confirmed that the paper-based, nucleic acid-detecting kit of the present invention perfectly coincided with the results obtained using the Roche Cobas 4800HPV test, it can be seen that the paper-based, nucleic acid-detecting kit of the present invention is excellent in reproducibility and accuracy.

Although specific parts of the present invention have been described in detail, it is obvious to those skilled in the art that such specific descriptions are only preferred embodiments and the scope of the present invention is not limited thereby. Accordingly, the substantial scope of the present invention will be defined by the appended claims and equivalents thereof.

INDUSTRIAL APPLICABILITY

The present invention relates to a paper-based, nucleic acid-detecting sensor capable of easily and simply detecting the presence of a target nucleic acid and a method for detecting a nucleic acid using the same, and according to the present invention, the presence or absence of the target nucleic acid can be easily, quickly, and simply detected compared to an existing method, so that the present invention is industrially applicable.

---

The invention claimed is:

1. A paper-based, nucleic acid-detecting sensor consisting of:

a negatively-charged porous first paper substrate;

a separation layer stacked on one surface of the first paper substrate and comprising Sepharose beads and glass beads; and a negatively-charged porous second paper substrate stacked on one surface of the separation layer;

wherein, when a labeled PCR amplicon and a capture nanoparticle are added onto the second paper substrate, the labeled PCR amplicon and the captured nanoparticle move through the second paper substrate and pass to the separation layer in this order;

wherein the labeled PCR amplicon comprises a label selected from the group consisting of avidin, biotin, avidin-biotin, an antigen, a target molecule, and an oligonucleotide;

wherein the capture nanoparticle is coated with a capture molecule capable of binding the label of the PCR amplicon, and wherein the capture molecule is selected from the group consisting of avidin, streptavidin, an antibody, an aptamer, and an oligonucleotide;

wherein the first paper substrate is for visualizing, with the naked eye, a complex formed between a labeled target nucleic acid in the PCR amplicon and the coated capture nanoparticle that spreads on the first paper substrate after passing through the separation layer without staying in the separation layer; and wherein a total area of the second paper substrate is 2 to 10 times smaller than a total area of the first paper substrate.

2. The paper-based, nucleic acid-detecting sensor of claim 1, wherein pores of the first paper substrate and pores of the second paper substrate are the same sizes.

3. The paper-based, nucleic acid-detecting sensor of claim 2, wherein the pores have a size of 2.3 μm.

4. The paper-based, nucleic acid-detecting sensor of claim 1, wherein the separation layer has a thickness of 10 to 100 μm.

5. A paper-based, nucleic acid-detecting kit comprising:

a) a first solution in which capture nanoparticles subjected to coating treatment with a coating selected from the group consisting of avidin, streptavidin, an antibody capable of being bound to an antigen bound to a primer by an antigen-antibody reaction, an aptamer that specifically binds to a target molecule bound to a primer and an oligonucleotide complementary to an oligonucleotide bound to a primer are dispersed; and b) the paper-based, nucleic acid-detecting sensor of claim 1.

6. The paper-based, nucleic acid-detecting kit of claim 5, wherein the nanoparticle is selected from the group consisting of a magnetic bead, a gold (Au) nanoparticle, a silver (Ag) nanoparticle, a platinum (Pt) nanoparticle, a quantum dot, an upconversion nanoparticle (UCNP) graphene-nanoparticle complex, a color dyed particle, and a latex nanoparticle.

7. The paper-based, nucleic acid-detecting kit of claim 5, wherein the nanoparticles are magnetic beads coated with streptavidin.

8. The paper-based, nucleic acid-detecting kit of claim 5, further comprising a-1) a primer set that specifically binds to a target nucleic acid to be detected, wherein the primer set comprises a forward primer labeled with a label selected from the group consisting of avidin, biotin, avidin-biotin, an antigen, a target molecule and an oligonucleotide, and a reverse primer labeled with fluorescence.

9. A method for analyzing a PCR amplicon, the method comprising:

(a) obtaining a reaction product by mixing the first solution of the paper-based, nucleic acid-detecting kit of claim 5 with a PCR amplicon labeled with any one selected from the group consisting of avidin, biotin, avidin-biotin, an antigen, a target molecule, and an oligonucleotide; and (b) adding the reaction product dropwise to the sensor of the paper-based, nucleic acid-detecting kit of claim 5.

10. The method of claim 9, after Step (b), further comprising (c) determining whether or not a target nucleic acid is present in the PCR amplicon through the range of the reaction product spread on the surface of the first paper substrate of the sensor.

11. The method of claim 9, wherein Step a) comprises:

a-1) extracting a nucleic acid from a biological sample separated from a specimen to be tested; and a-2) obtaining a PCR amplicon comprising a target nucleic acid, wherein the PCR amplicon is obtained using a primer set comprising:

a forward primer labeled with avidin, biotin, avidin-biotin, an antigen, a target molecule, or an oligonucleotide, and a reverse primer labeled with a fluorescent label.

* * * * *